(12) United States Patent
Willliams

(10) Patent No.: US 7,964,098 B2
(45) Date of Patent: Jun. 21, 2011

(54) APPARATUS AND METHOD FOR FILTERING BIOLOGICAL SAMPLES

(75) Inventor: Richard O. Willliams, Vancouver, WA (US)

(73) Assignee: Alpha-Tec Systems, Inc., Vancouver, WA (US)

( * ) Notice: Subject to any disclaimer, the term of this patent is extended or adjusted under 35 U.S.C. 154(b) by 1171 days.

(21) Appl. No.: 11/671,626

(22) Filed: Feb. 6, 2007

(65) Prior Publication Data

US 2008/0185349 A1  Aug. 7, 2008

(51) Int. Cl.
*B01D 35/02* (2006.01)
*B01D 35/01* (2006.01)
*B01D 35/22* (2006.01)
*B01D 29/00* (2006.01)

(52) U.S. Cl. ......... 210/232; 210/474; 210/482; 210/767
(58) Field of Classification Search .................. 210/232, 210/474, 482, 767; 422/101
See application file for complete search history.

(56) References Cited

U.S. PATENT DOCUMENTS

| | | | |
|---|---|---|---|
| 4,081,356 A | 3/1978 | Zierdt | |
| 4,675,110 A | 6/1987 | Fay | |
| 5,489,385 A * | 2/1996 | Raabe et al. | 210/448 |
| 5,503,801 A * | 4/1996 | Brugger | 422/44 |
| 5,556,544 A | 9/1996 | Didier | |
| 5,591,251 A * | 1/1997 | Brugger | 95/242 |
| 5,624,554 A | 4/1997 | Faulkner et al. | |
| 5,925,250 A * | 7/1999 | Rocha | 210/436 |
| 6,296,763 B1 | 10/2001 | Hicks | |
| 6,468,427 B1 * | 10/2002 | Frey | 210/497.01 |
| 2003/0006187 A1 * | 1/2003 | Frey | 210/497.01 |
| 2004/0005246 A1 | 1/2004 | Efthimiadis et al. | |
| 2004/0038425 A1 | 2/2004 | Ferguson et al. | |
| 2006/0254972 A1 | 11/2006 | Tai et al. | |

* cited by examiner

*Primary Examiner* — Thomas M Lithgow
(74) *Attorney, Agent, or Firm* — Marger Johnson & McCollom, P.C.

(57) ABSTRACT

An apparatus and method for filtering a biological sample is presented. The apparatus comprises a body member has an upper end and a lower end and defining a workspace therewithin. A first attachment portion is integrally joined to the lower end of the body member for interlockingly receiving a filtered sample container. A second attachment portion is integrally joined to the upper end of the body member for interlockingly receiving a sample transport container. A substantially conically-shaped filter member, located within the workspace, is integrally joined to the lower end of the body member and extends upwardly above the lower end of the body member toward the upper end of the body member. The filter member defines a plurality of openings in its upwardly extending portion.

20 Claims, 1 Drawing Sheet

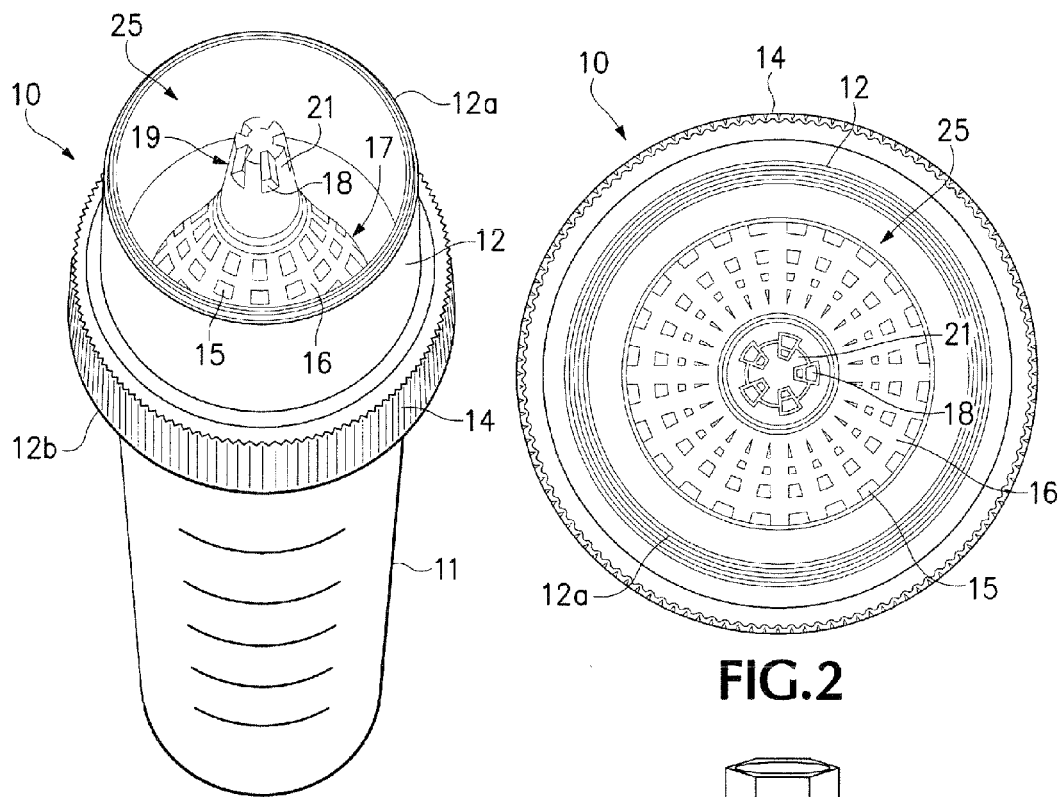
FIG.1
FIG.2
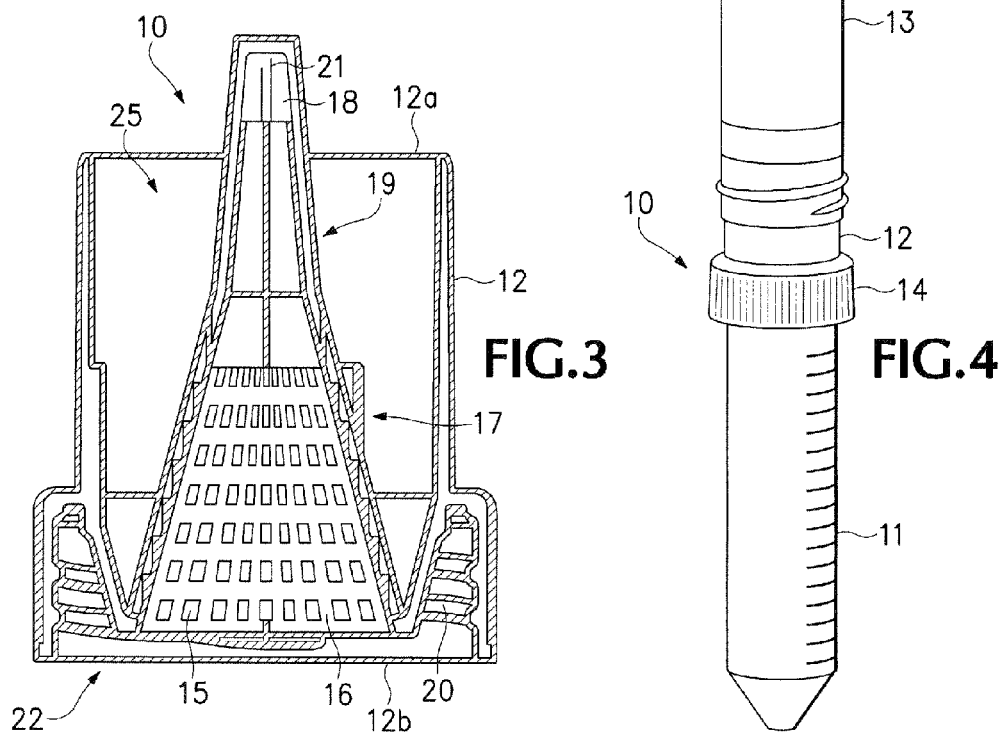
FIG.3
FIG.4

APPARATUS AND METHOD FOR FILTERING BIOLOGICAL SAMPLES

BACKGROUND OF THE INVENTION

This invention relates to an apparatus and a method for filtering biological samples. More specifically, an apparatus and a method can be provided for the filtration of biological samples via gravitational filtration techniques.

One field of gravitational filtration is the separation of parasites and parasite eggs from fecal samples. In the past, this area of technology has relied upon a variety of filtration techniques and filtration apparatus. These separation procedures have typically been categorized as either closed or open.

An open filtration procedure relates to one in which sample is poured from a specimen collection container into a apparatus containing a filter of some type, usually gauze or an integral screen, in order to separate solid particulate matter from the liquid. The separated liquid typically includes parasitic objects including eggs and larva. This filtering apparatus is placed on top of a desired container which collects the filtered liquid portion of the fecal sample.

The term closed filter procedure refers one which utilizes a filtering apparatus designed to interconnect both the sample collection container and the intended receiving container for the filtered liquid portion of the sample. Using this sort of apparatus one can interconnect the sample collection and the transport container to the intended container so that they are in communication with each other. Then, one can allow gravity or centrifugation to accomplish filtration rather than by active sample pouring.

Closed procedures allow those performing fecal parasite separation and concentration procedures to avoid the potential for spilling and contamination which are inherent in open procedures. They also minimize the odor associated with processing fecal specimens. The prior art closed techniques have however suffered from several shortcomings. The filter units of closed fecal filtration apparatus tend to become clogged or blocked with particulate fecal matter. This clogging creates a pressure imbalance characterized by the inability of gas to pass between the destination container and the sample container. The inability to equalize gas pressure prevents liquid from flowing into the destination container and halts the filtration process. Additionally closed filtration apparatus typically have a flat filter section with a small surface area compared to the volume of the introduced fecal sample. This proportionally small surface area ratio slows the sample filtration and can even restrict flow entirely.

None of the prior art solutions has been completely effective at overcoming the habit of clogging with particulate fecal matter and none has addressed the inadequate surface area provided by a flat filter that is limited in area by the restrictions imposed by the diameter of the commercially available centrifuge tubes used as containers.

U.S. Pat. No. 4,081,356 discloses a filter apparatus for closed filtration of a fecal sample with a threaded attachment to a commercially available centrifuge tube, a flat circular filter, a central but non-integral tube for gas flow, and a cylindrical friction attachment point for a commercially available standard patient specimen transport container. In this technology the small non-integral gas exchange tube can easily become occluded or pushed into the container tube causing pressure imbalance and interruption of filtration. The filter of this technology is a flat disc with the approximate diameter of a commercially available centrifuge tube.

U.S. Pat. No. 4,675,110 discloses a filter apparatus for closed filtration of a fecal sample with a threaded attachment to commercially available centrifuge tube, a flat circular filter, and peripheral gas exchange channels arrayed in a circular pattern along a bordering lip which is positioned perpendicular to the downward flow of the patient sample. The gas exchange channels in this apparatus are by necessity small to prevent passing particulate fecal matter but are resultantly prone to clogging. The filter is a flat disc with the approximate diameter of a commercially available centrifuge tube.

U.S. Pat. No. 5,556,544 discloses a filter apparatus for closed filtration of a fecal sample with a threaded attachment to a commercially available centrifuge tube, a flat circular filter, a central but integral stem for air gas flow, and a cylindrical friction attachment point for a commercially available standard patient specimen transport container. The air exchange stem in this technology is integral to the filter apparatus but still below the potential level of the liquid created by the addition of the sample to the filtration apparatus and still therefore subject to clogging. The filter of this technology is a flat disc with the approximate diameter of a commercially available centrifuge tube. U.S. Pat. No. 5,925,250 is similar to U.S. Pat. No. 5,556,544 except for an outward sheath which prevents cross contamination.

U.S. Pat. No. 5,624,554 discloses a filter apparatus which is integral to and provided with the cap of a patient sample collection and transport container. This apparatus integrates specimen collection and filtration but relies on positive pressure to force specimen filtration. Therefore, this apparatus is subject to potential clogging, leaking, and spraying.

U.S. Pat. No. 6,296,763 discloses a system for closed filtration which encompasses a unique specimen collection tube, filtration apparatus, and container tube. The filtration method in the preferred embodiment of this system is via centrifugation and therefore requires special equipment.

SUMMARY OF THE INVENTION

This invention overcomes the limitations of previous closed filtration systems comprising a sample container and a transport container. This invention relates in general to an apparatus and method for processing biological samples by filtration techniques. In one embodiment, filtration is accomplished by trapping large particulate matter in the samples while passing parasitic elements within a liquid portion of the sample into a sample container. Another embodiment relates to fecal sample filtration for the concentration and recovery of parasites. A further embodiment permits substantially uninhibited airflow between the sample container and the transport container by allowing for pressure equalization thus preventing the termination of the filtration process. Still another embodiment provides for substantially unobstructed gas passage between the transport container and the sample container. In still a further embodiment the surface area of the filter barrier is expanded to promote rapid sample flow and resist clogging.

An apparatus is provided for filtering a biological sample. The apparatus comprises a body member having an upper end and a lower end and defining a workspace therewithin. In one embodiment a substantially cylindrical body member is provided.

A substantially conically-shaped filter member is located within the workspace. The filter member is integrally joined to the lower end of the body member and extends upwardly above the lower end of the body member toward the upper end of the body member. The filter member defines a plurality of openings in its upwardly extending portion.

A first attachment portion is integrally joined to the lower end of the body member for interlockingly receiving a filtered sample container. A second attachment portion is integrally joined to the upper end of the body member for interlockingly receiving a sample transport container.

In one embodiment, the diameter of lower end of the filter member is greater than the diameter of the upper end of the filter member. In a further embodiment, the filter member comprises an elongate-shaped conical filter member.

In one embodiment the apparatus comprise rectangularly-shaped openings. In another embodiment, the openings comprise elongate rectangularly-shaped openings. In still another embodiment, the height of the rectangularly-shaped openings are greater than the width of the rectangularly-shaped openings. In a further embodiment, the openings are arranged radially in arrays of rows. In still a further embodiment, the openings are arranged radially in arrays of parallel rows. In an additional embodiment, the openings substantially completely surround the filter member. In a further additional embodiment, the openings extend above the lower end of the filter member. In still an additional embodiment, the width of opening can be equal to or less than height of the opening.

In one embodiment, the biological sample is a fecal specimen. In another embodiment, the fecal specimen is suspended in a diluent liquid.

In an embodiment herein, a hollow gas exchange stem is joined to the distal end of the filter member. In an additional embodiment, the gas exchange stem is a conically-shaped gas exchange stem. In a still additional embodiment, the gas exchange stem is an elongate conically-shaped gas exchange stem. In a further embodiment, the diameter of lower end of the gas exchange stem is greater than the diameter of the upper end of the gas exchange stem.

In one embodiment, the hollow gas exchange stem can protrude beyond the upper end of the cylindrical body member. In another embodiment, the hollow gas exchange stem includes a plurality of gas exchange vents positioned at the distal end of the gas exchange stem so that the gas exchange stem vents exchange gas therethrough.

In a further embodiment, gas exchange vents are arrayed radially around the distal end of the gas exchange stem. In still a further embodiment, the gas exchange vents comprise open passages through the gas exchange stem arranged along an axis parallel to longitudinal axis of the gas exchange tube. In yet a further embodiment, the gas exchange vents are arranged in an inclined position, typically conically-shaped, to more effectively prevent clogging by the biological samples.

In one embodiment, at least about 10% of the total area of the upwardly extending portion of the filter member comprises openings. In another embodiment, at least about 15% of the total area of the upwardly extending portion of the filter member comprises openings. In still another embodiment, at least about 20% of the total area of the upwardly extending portion of the filter member comprises openings. In yet another embodiment, at least about 25% of the total area of the upwardly extending portion of the filter member comprises openings.

In one embodiment, the apparatus has a filter surface including opening of up to about 90% of the total area of the filter member. In another embodiment, the apparatus has a filter surface including opening of up to about 80% of the total area of the filter member. In still another embodiment, the apparatus has a filter surface including opening of up to about 70% of the total area of the filter member. In yet another embodiment, the apparatus has a filter surface including opening of up to about 60% of the total area of the filter member.

A method for filtering a biological sample is also provided. The method comprises providing an apparatus for filtering a biological sample. The apparatus comprises a body member having an upper end and a lower end and defines a workspace therewithin. A substantially conically-shaped filter member is located within the workspace which is integrally joined to the lower end of the body member and which extends upwardly toward the upper end of the body member. The filter member defines a plurality of openings in its upwardly extending portion.

A filtered sample container is interlockingly attached to the lower end of the body member. An upright sample transport container is provided containing an unfiltered biological sample. The upper end of the body member of the apparatus is inverted and attached to the upright sample transport container. Then, the attached apparatus and sample transport container are inverted so that the unfiltered biological sample flows through the openings and a filtered biological sample is introduced and is collected in the filtered sample container.

BRIEF DESCRIPTION OF THE DRAWINGS

FIG. 1 is an overhead perspective view of an apparatus for filtering biological samples connected to a filtered sample container.

FIG. 2 is a plan view of the apparatus of FIG. 1.

FIG. 3 is a sectional view of the apparatus taken along line 3-3 of FIG. 2.

FIG. 4 is a side perspective view of an apparatus for filtering biological samples connected at one end to a filtered sample container and at the other end to a sample transport container.

DETAILED DESCRIPTION

FIGS. 1-4 show an apparatus 10 for filtering biological samples which is attachable to a filtered sample container 11 (see FIGS. 1 and 4). Apparatus 10 can be employed for the filtration of fecal specimens suspended in a transport liquid. The body member 12 of the apparatus 10 as depicted is substantially cylindrical in shape, includes upper end 12a and lower end 12b, and defines a work space 25. Apparatus 10 as depicted in FIGS. 1-4 is comprised certain integral portions. A threaded attachment portion 22 can be designed to mate with the threads of filtered sample container 11, typically a commercial centrifuge tube. A substantially conically-shaped filter 17 can be located within workspace 25. A hollow gas exchange stem 19 forms the distal end of the cone shaped filter unit. A radial array of gas exchange vents 15 are disposed at the distal end of the gas exchange stem 19.

The upper and lower ends 12a, 12b of the body member 12 are employed as respective attachment points for the filtered sample container 11 and the sample transport container 13. The filtered sample container 11 can be connected by threaded attachment and the sample transport container 13 can be connected by frictional attachment. The friction attachment of sample transport container 13 can be accomplished via a body member 12 having a smooth outer surface. In this way, the apparatus 10 can be used in conjunction with, for example, standard thirty milliliter transport vials. This connection will occur by the friction mating of the internal surface of sample transport container 13 with the outer surface of the body member 12. This friction mating will be caused by opposing inward pressure and twisting motion until a liquid tight seal can be created. This frictional attachment can occur parallel to, and in opposite direction from, the threaded filtered sample container attachment in order to facilitate the requisite level of fixed engagement during the filtering of the biological sample.

The second attachment is the threaded filtered sample container attachment, which employs the lower end 12b. The external portion of lower end 12b can include a frictional gripping surface 14 which can be used to promote grasping of the body member 12 during the threaded mating and un-mating attachment operation to filtered sample container 11. The internal portion of the lower end 12b can be comprised of female threads 20 which fittingly engage the male threads of filtered sample container 11, such as the male threads found on commercial centrifuge tubes. The mating between female threads 20 and filtered sample container 11 occurs when a liquid tight seal can be formed.

Conically-shaped filter 17 and hollow gas exchange stem 19 together extend in the same direction toward upper end 12a within workspace 25. The surface of the filter 17 can be conical in shape. Preferably, filter 17 comprises steeply inclined walls to provide for a greater filter surface area. The surface of the filter 17 includes openings 15 which are defined within a solid filter network 16 which is oriented vertically along the length of the filter 17 and horizontally around the diameter of the filter 17. The distal end of conical filter 17 is joined by gas exchange stem 19. This gas exchange stem can be formed by a hollow tube which can be vented at its apex with a plurality of radially arranged gas exchange vents 18. These gas exchange vents 18 are oriented vertically extending from near the distal end of the distal end downward toward the base of the filter 17. The tubular grid 21 which defines the gas exchange vents 18 can be oriented at the steep angle of the conical shape to allow for potentially clogging debris to slide away from these vents.

In use, a patient biological sample, such as a fecal sample to be examined for parasitic infestation, can be collected in a sample transport container, typically a transport vial containing a transport liquid. The transport liquid can be a fixative or other diluent liquid. For the performance of several diagnostic procedures the liquid portion of this specimen, along with any parasite larva and eggs present, must be separated from particulate matter which can be composed of undigested food and debris.

By employing the apparatus 10, this separation can be carried out through gravitational filtration. To accomplish this, filtered sample container 11 can be attached to apparatus 10. The cap can be removed from the sample transport container 13 which houses a biological sample, which can be in the form of a specimen transport liquid suspension, and the apparatus 10 and filtered sample container 11 are inserted into the open end of the sample transport container 13 containing the specimen for filtration. To secure a liquid tight seal the apparatus 10 can be pressured into the the sample transport container 13 with a slight twisting motion until tight. The sample transport container 13, apparatus 10, and filtered sample container 11 can be then inverted so that the centrifuge tube can be at the lowest point of a vertical arrangement. The liquid portion of the sample which can be a transport solution, parasitic eggs and larva, and very small particulate matter that forms a non-viscous suspension, will then pass through the openings 15 of the filter 17 and flow into the filtered sample container 11. The large particulate matter such as undigested food will be trapped by the solid filter network 16 of the filter 17.

To equalize gas pressure during this process and prevent filter 17 blockage created by a pressure differential, gas will flow freely between the filtered sample container 11 and the sample transport container 13 through the integral gas exchange stem 19. Gas exchange can be ensured since the gas exchange vents 18 are on the distal end of the gas exchange stem 19 which, when inverted and inundated the with biological sample transport solution mixture, extends beyond the level which would be reached by a volume typical for this operation. Any particulate and potentially obstructing biological matter which lands on the gas exchange stem by happenstance will slide clear of the gas exchange vents 18 due the inclined nature of the tubular grid 21. After filtration, the filtration apparatus 10, and the sample transport container 13 containing filtered particulate matter can be unthreaded from the filtered sample container 11 and discarded.

Speed and efficiency of sample filtration can be increased due to the increased surface area of the filter 17 as compared to a flat circular filter. In one embodiment, the filter 17 provides at least about 1.5 times, in another embodiment at least about 2.0 times, and in a further embodiment at least about 2.5 times, the surface area of a flat circular filter of equal diameter. This increased surface area for filtration allows for greater proportional contact between the biological sample and filter 17 allowing more liquid to flow directly between containers 11 and 12 without obstruction due to the formation of a layer of particulate matter.

The subject method allows for ease of use. When these containers 11 and 12 are joined together, filtration can be accomplished via simple inversion so that the biological sample, driven by gravity, flows from the container 13 through the filter into the container 11 leaving behind particulate matter. This process occurs with no agitation and in a brief period of time. The efficiency of use this design provides coupled with the fact that no specialty equipment can be required for operation creates a apparatus that can be effortlessly used by those familiar with technologies such as fecal parasitology filtration.

The apparatus 10 can be fabricated from a polymeric material, more particularly a thermoplastic polymeric material. Examples of the polymeric material which can be employed in producing apparatus 10 (and containers 11 and 12 as well) are polyolefins such as conventional and linear polyethylene (LDPE & HDPE), polypropylene, PMP (polymethylpentene), TPX, styrene resins such as polystyrene and high-impact polystyrene, acrylonitriles, acrylonitrile-styrene, vinyl resins such as polyvinyl chlorides, polycarbonates, and acetals/acetyls such as polyoximethylene and polyformaldehyde.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

I claim:

1. An apparatus for filtering a fecal specimen biological sample comprising:
   a body member having an upper end and a lower end and defining a workspace therewithin;
   a first attachment portion integrally joined to the lower end of the body member for interlockingly receiving a filtered sample container;
   a second attachment portion integrally joined to the upper end of the body member for interlockingly receiving a sample transport container;

a substantially elongate conically-shaped fecal specimen filter member located within said workspace, the height of the filter member being greater than the width of the filter member and forming a steeply inclined wall to provide for an increased filter surface area, the filter member being integrally joined to the lower end of the body member and extending upwardly above said lower end of the body member toward said upper end of the body member, the filter member defining a plurality of openings in its upwardly extending portion; and an elongate conically-shaped hollow gas exchange stem joined to the distal end of said filter member for exchanging gas therethrough, said gas exchange stem further including a plurality of gas exchange vents positioned at the distal end of the gas exchange stem, said gas exchange stem vents exchanging gas therethrough, and said gas exchange stem and said gas exchange stem vents, respectively, being oriented at a steep angle of the conical shape to allow for a potentially clogging fecal specimen to slide away from said gas exchange vents and thereby prevent clogging.

2. The apparatus of claim 1, wherein the diameter of lower end of the filter member is greater than the diameter of the upper end of the filter member.

3. The apparatus of claim 1, which has a filter surface including opening of up to about 90% of the total area of the filter member.

4. The apparatus of claim 1, where in the openings comprise rectangularly-shaped openings.

5. The apparatus of claim 1, where in the openings comprise elongate rectangularly-shaped openings.

6. The apparatus of claim 4, where in the height of the rectangularly-shaped openings are greater than the width of the rectangularly-shaped openings.

7. The apparatus of claim 1, wherein the openings are arranged radially in arrays of rows.

8. The apparatus of claim 1, wherein the openings are arranged radially in arrays of parallel rows.

9. The apparatus of claim 1, wherein the diameter of lower end of the gas exchange stem is greater than the diameter of the upper end of the gas exchange stem.

10. The apparatus of claim 1, wherein at least about 10% of the total area of the upwardly extending portion of the filter member comprises openings.

11. The apparatus of claim 1, wherein said hollow gas exchange stem protrudes beyond the upper end of the cylindrical body member.

12. The apparatus of claim 1, wherein gas exchange vents are arrayed radially around the distal end of the gas exchange stem.

13. The apparatus of claim 1, wherein the gas exchange vents comprise open passages through the gas exchange stem arranged along an axis parallel to longitudinal axis of the gas exchange tube.

14. A method for filtering a fecal specimen biological sample comprising:

providing an apparatus for filtering a biological sample comprising a body member having an upper end and a lower end and defining a workspace therewithin, a substantially elongate conically-shaped fecal specimen filter member located within said workspace, forming a steeply inclined wall to provide for a greater filter surface areas, the height of the filter member being greater than the width of the filter member and forming a steeply inclined wall to provide for an increased filter surface area, the filter member being integrally joined to the lower end of the body member and extending upwardly above said lower end of the body member toward said upper end of the body member, the filter member defining a plurality of openings in its upwardly extending portion;

providing an elongate conically-shaped hollow gas exchange stem joined to the distal end of said filter member for exchanging gas therethrough, said gas exchange stem further including a plurality of gas exchange vents positioned at the distal end of the gas exchange stem, said gas exchange stem vents exchanging gas therethrough, and said gas exchange stem and said gas exchange stem vents, respectively, being oriented at a steep angle of the conical shape to allow for a potentially clogging fecal specimen to slide away from said gas exchange vents and thereby prevent clogging;

interlockingly attaching a filtered sample container to the lower end of the body member;

providing an upright sample transport container containing an unfiltered biological sample;

inverting and attaching the upper end of the body member of the apparatus to the upright sample transport container; and inverting the attached apparatus and sample transport container so the unfiltered biological sample flows through the openings and a filtered biological sample is introduced and is collected in the filtered sample container.

15. The method of claim 14, wherein the diameter of lower end of the filter member is greater than the diameter of the upper end of the filter member.

16. The method of claim 14, where in the openings comprise rectangularly-shaped openings.

17. The method of claim 14, where in the height of the rectangularly-shaped openings are greater than the width of the rectangularly-shaped openings.

18. The method of claim 14, wherein gas exchange vents are arrayed radially around the distal end of the gas exchange stem.

19. The method of claim 14, wherein the gas exchange vents comprise open passages through the gas exchange stem arranged along an axis parallel to longitudinal axis of the gas exchange tube.

20. The method of claim 14, wherein the diameter of lower end of the gas exchange stem is greater than the diameter of the upper end of the gas exchange stem.

* * * * *

UNITED STATES PATENT AND TRADEMARK OFFICE
CERTIFICATE OF CORRECTION

| | | |
|---|---|---|
| PATENT NO. | : 7,964,098 B2 | Page 1 of 1 |
| APPLICATION NO. | : 11/671626 | |
| DATED | : June 21, 2011 | |
| INVENTOR(S) | : Richard O. Williams | |

It is certified that error appears in the above-identified patent and that said Letters Patent is hereby corrected as shown below:

In the Claims:

On Column 8, line 43, claim 17, the words "The method of claim 14..." should read -- The method of claim 16... --.

Signed and Sealed this
Sixth Day of August, 2013

Teresa Stanek Rea
*Acting Director of the United States Patent and Trademark Office*